United States Patent [19]

Hansen et al.

[11] 4,002,170
[45] Jan. 11, 1977

[54] ANTICOAGULANT DELIVERY MEANS FOR ASPIRATION WAND

[75] Inventors: A. Boyd Hansen; Gordon S. Reynolds, both of Bountiful, Utah

[73] Assignee: Sorenson Research Co., Inc., Salt Lake City, Utah

[22] Filed: Aug. 25, 1975

[21] Appl. No.: 607,407

Related U.S. Application Data

[63] Continuation-in-part of Ser. No. 514,055, Oct. 11, 1974, Pat. No. 3,955,573.

[52] U.S. Cl. .............................................. 128/276
[51] Int. Cl.² ......................................... A61M 1/00
[58] Field of Search .......................... 128/276–278, 128/214 R, 214.2, 348, 350 R, 240

[56] References Cited

UNITED STATES PATENTS

| 2,804,075 | 8/1957 | Borden | 128/277 |
| 3,807,401 | 4/1974 | Riggle et al. | 128/277 |
| 3,955,573 | 5/1976 | Hansen et al. | 128/276 |

Primary Examiner—Dalton L. Truluck
Attorney, Agent, or Firm—H. Ross Workman; J. Winslow Young

[57] ABSTRACT

An anticoagulant delivery device forming part of an aspiration wand for use in connection with autologous blood transfusion wherein an anticoagulant is delivered along essentially the entire internal periphery of the aspiration wand in the vicinity of the aspiration tip and intimately mixed with aspirated blood.

4 Claims, 3 Drawing Figures

ANTICOAGULANT DELIVERY MEANS FOR ASPIRATION WAND

BACKGROUND

Related Application

This application is a continuation-in-part of my copending U.S. patent application Ser. No. 514,055, filed Oct. 11, 1974 U.S. Pat. No. 3,955,573.

1. Field of the Invention

This invention relates to autologous blood transfusion and more particularly to an improved anticoagulant delivery device.

2. The Prior Art

Autologous blood transfusion is commonly defined as the return of the patient's blood to his own circulatory system during an active bleeding episode such as encountered in certain forms of surgery. It is well known that conventional homologous blood transfusion involves a high risk of hemagglutination, disease transfer and other undesirable side effects. Hemagglutination is minimized by lengthy and expensive blood cross-match procedures. Even with cross-matching, however, transfusion reactions are undesirably frequent. Presently, there is no known practical way of detecting and preventing transmittal of diseases such as hepatitis through homologous blood transfusion. Autologous blood transfusion has the distinct advantage in that adverse serum reactions are completely eliminated along with other problems suggested above associated with blood transfusions.

While blood replacement through autologous blood transfusion has been demonstrated to be safe and effective, routine use of this technique has not been established. One obvious reason for this failure is the lack of an effective, practical, inexpensive, and efficient method and apparatus for recovering and treating the blood for reinfusion.

During the collection phase, one of the most vital considerations is the prevention of coagulation of the aspirated blood. It is known that blood quickly commences to initiate coagulation upon exposure to the atmosphere or contact with a foreign body. Accordingly, devices for aspirating blood wherein anticoagulant is introduced into the blood at a substantial distance from the point of blood entry tend to permit unnecessary blood coagulation. An example of such a device is disclosed in U.S. Pat. No. 3,807,401.

Another system for preventing blood coagulation includes chamber anticoagulation which involves the constant surveillance and administration of anticoagulant to a collection chamber. This technique does not prevent clot formation in the vacuum line between the suction tip and the collection chamber. Further, devices which introduce rapid pressure change and/or abrade the blood cells cause hemolysis of the blood making it undesirable for reinfusion purposes.

Wands or "sucker tips" which are used to aspirate blood during surgery for removal to a remote container are well known in the art. They conventionally include a handle, aspiration tip and a long tube into which a vacuum is introduced to draw aspirated blood to the container. Until this present invention, there has been no practical way to introduce anticoagulant into the blood immediately upon aspiration of the blood and without hemolysis or other undesirable side effects.

BRIEF SUMMARY AND OBJECTS OF THE INVENTION

The present invention avoids unnecessary coagulation of blood aspirated from the patient in conjunction with autologous blood transfusion by coating the interior periphery of the wand with anticoagulant thereby minimizing clot formation upon contact of the blood with the interior of the wand at the time of aspiration. The invention includes an aspiration wand having a probe terminating in a perforated tip and including a mixing chamber adjacent the perforated tip. Anticoagulant is introduced into the aspirated blood through an annular channel located near the tip and adapted to deliver anticoagulant along the internal periphery of the wand so as to coat the interior of the wand with anticoagulant and thoroughly mix the anticoagulant with the blood in the mixing chamber prior to transport through the suction line to a collection reservoir.

It is therefore an object of the present invention to provide improvements in the art of aspirating blood for autologous transfusion.

It is another object of this invention to provide an aspiration wand wherein an anticoagulant is delivered around the internal periphery of the aspiration wand.

An even still further object of this invention is to provide apparatus and method wherein anticoagulant is intimately mixed with the aspirated blood in a mixing chamber immediately adjacent the point of aspiration.

These and other objects and features of the present invention will become more fully apparent from the following description and appended claims taken in conjunction with the accompanying drawing.

DETAILED DESCRIPTION OF THE PREFERRED EMBODIMENT

Figure 1:
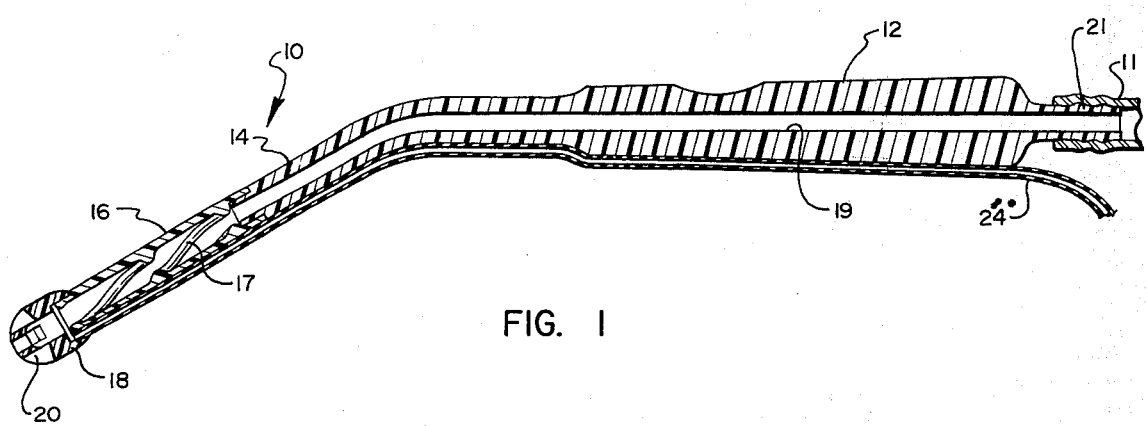
FIG. 1 is a longitudinal cross-sectional view of one presently preferred embodiment of the present invention.
Figure 2:
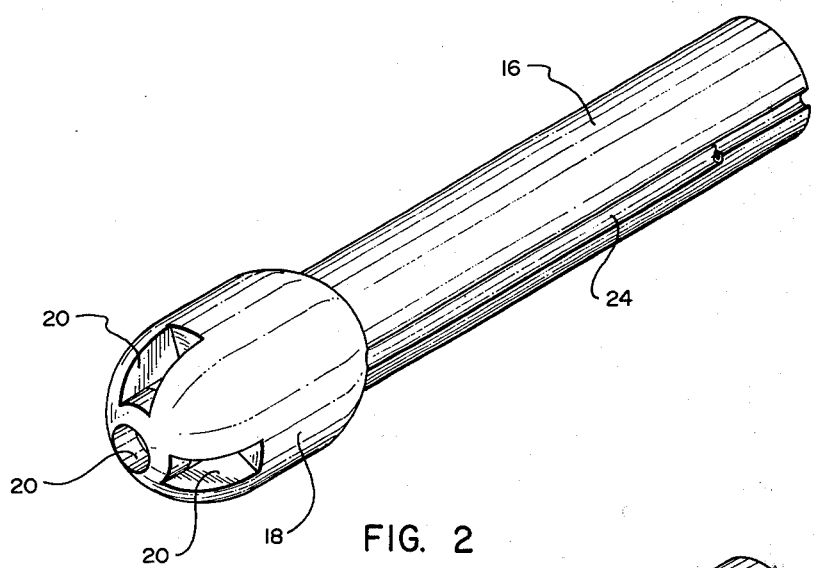
FIG. 2 is a fragmentary perspective view of a preferred embodiment of the suction tip of the aspiration wand of FIG. 1.

The invention is best understood by reference to the figures wherein like parts are designated with like numerals throughout.

The anticoagulant delivery unit disclosed herein is particularly useful in conjunction with the Aseptic Suction Collection System and Method, U.S. Pat. No. 3,866,608. Of course, any suitable blood collection reservoir could be used with the illustrated embodiments of the invention. In general, blood is aspirated through a wand generally designated 10 and is delivered by blood line 11 into a suitable receptacle (not shown) for storage and later reinfusion into the patient according to acceptable techniques of autologous blood transfer.

The aspiration wand 10 includes a handle 12 and an integral probe 14. In the presently preferred embodiments of the present invention the handle 12, probe 14 and mixing chamber 16 are fabricated from medical grade plastic material so as to be easily fabricated, inexpensive, sterilizable, and disposable. Probe 14 terminates in a rounded tip 18 having ports 20 therein.

The handle 12, probe 14 and tip 18 define a continuous hollow passageway 19 traversing the entire length of the wand 10. The handle 12 has a rearwardly projecting male coupling 21 onto which the conventional vacuum blood line 11 is press-fit. Probe 14 also includes a mixing chamber 16 located adjacent the tip 18. The mixing chamber 16 is, in the illustrated embodiment, a cylindrical extension of the probe 14 and is hollow to permit internal mixing of blood and anticoagulant and subsequent transport of the blood to a container (not shown).

In FIG. 1, the mixing chamber 16 is shown to be press-fit onto both the probe 14 and the tip 18. If desired, the mixing chamber can be bonded or form an integral part of the probe and/or the tip 18. The mixing chamber 16 may have any suitable configuration such as those described and claimed in the aforementioned patent application Ser. No. 514,055 filed Oct. 11, 1974. In the embodiment of FIG. 1, the mixing chamber 16 includes spiralling ribs 17 which provide for mechanical mixing of blood aspirated through port 20 with an anticoagulant delivered through tubing 24. Ribs 17 project into the interior of the pathway 19 and traverse a spiral path. Ribs 17 thus facilitate flow of the aspirated blood in a vortical manner so as to accommodate thorough mixing with anticoagulant and at the same time avoid significant pressure changes and cellular abrasion which tend to hemolyze blood cells.

Figure 3:
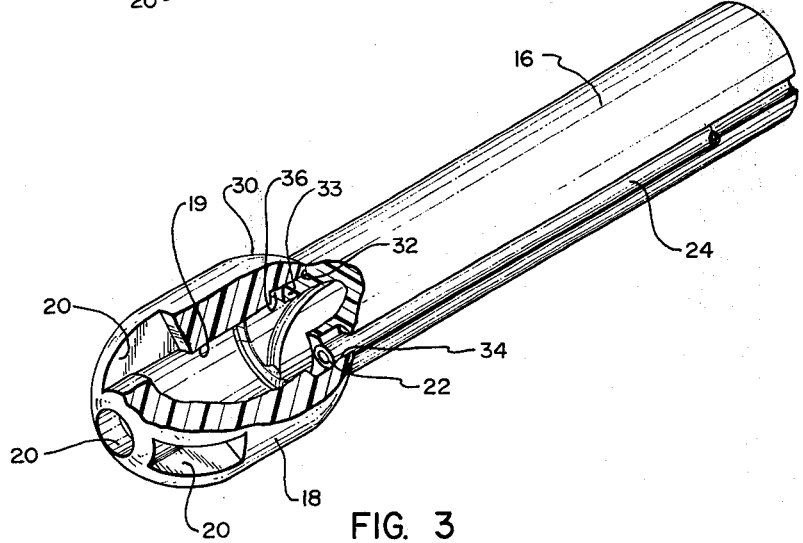
FIG. 3 is a fragmentary perspective view of the suction tip of FIG. 2, portions being broken away to reveal the annular channel.

Anticoagulant is preferably delivered to wand 10 near the base 30 of tip 18 and adjacent the mixing chamber 16 (see FIG. 3). While it is acknowledged that other suitable sites for delivering anticoagulant are available, this location brings the aspirated blood into immediate contact with anticoagulant and is more simple to construct. The anticoagulant is delivered through tubing 24 which is conventionally attached to a source of a suitable anticoagulant (not shown) such as heparin or Citrate-Phosphate-Dextrose (CPD). The tubing 24 is preferably attached to the exterior of device 10 along essentially its entire length so that tubing 24 is kept out of the way during surgery. If desired, the tubing 24 could be interposed through the hollow passageway 19 and anchored therein so that the open tip thereof is secured between the ports 20 and the mixing chamber 16. Further, the tubing 24 could be formed within the structure of the handle 12 and probe 14.

Referring now more particularly to FIG. 3, the mixing chamber 16 has an annular shoulder 32 against which the trailing end 30 of the tip 18 abuts. An annular forward projection 33 extends beyond the shoulder 32 into the tip 18. The tip 18 has an annular recess 34 which is larger in the axial direction than the projection 33. Thus, when the tip 18 is seated upon the projection 33 and abuts the shoulder 32, an annular channel 36 exists between the mixing chamber 16 and the tip 18. The channel 36 is open along its entire length so as to traverse the arcuate path adjacent the internal periphery of the passageway 19 where the tip 18 meets the mixing chamber 16.

From continued reference to FIG. 3, it is apparent that the anticoagulant delivery tube 24 opens at 22 directly into the channel 36. Thus, the channel 36 is caused to fill with anticoagulant and, when overfilled, will flow the anticoagulant over the surface of the passageway 19. Thus, the anticoagulant will coat the surface of the passageway 19 and significantly reduce the incidence of clot formation in the aspiration wand. Further, since the anticoagulant is admitted immediately upstream from the mixing chamber 16, the blood and anticoagulant will be promptly and efficiently mixed prior to delivery to the receptacle (not shown).

While FIG. 3 illustrates the delivery of anticoagulant adjacent from the mixing chamber, if the mixing chamber is omitted, the probe 14 can be easily configurated to accommodate direct attachment to the tip 18 so as to form a channel substantially identical to channel 36.

To aspirate blood with wand 10, the operator, generally a surgeon or his assistant, activates a vacuum source (not shown) to impose a vacuum in line 11. Even before blood is aspirated, anticoagulant will fill the channel 36 and flow over the surface of passageway 19. Thereafter tip 18 is inserted into blood which accumulates during surgery. The vacuum in line 11 draws blood through ports 20 of tip 18. Simultaneously, additional anticoagulant is delivered through the tube 24 to channel 36 where it flows into passageway 19 and is thoroughly mixed with the blood by passage over ribs 17 in mixing chamber 16. The treated blood is then transported along the passageway 19 and through blood line 11 to a suitable collection reservoir (not shown).

While the channel 36 preferably traverses an arcuate path of 360° of the interior periphery of the wand 10, a shorter arc could be used. Any channel configuration which permits anticoagulant to flow over a substantial portion of the periphery of passageway 19 could be used.

It will be noted that in the described embodiment, the anticoagulant is delivered to the blood in the immediate vicinity of the perforated tip before the blood reaches the mixing chamber. According to the present invention, the blood traverses only a very short distance before it contacts the anticoagulant-treated mixing chamber and is thereafter suitably mixed with anticoagulant to greatly minimize the opportunities for clot formation. The blood aspiration system of this invention is, therefore, a simple device which greatly simplifies the aspiration and treatment of blood with anticoagulant so that the blood is then suitable for autologous blood transfusion.

The invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An anticoagulant delivery device for aspirating and treating blood during surgery comprising:
   a hollow conduit, the hollow of the conduit having a vacuum applied thereto and defining a pathway for the transport of aspirated blood;
   a perforated tip joined to the conduit and comprising a passageway facilitating aspiration of blood into the hollow of the conduit;
   a channel traversing an arcuate path and opening radially only into the hollow of the conduit in the vicinity of the tip; and
   means for delivering the anticoagulant into the channel at a point below the open side of the channel so as to insure flow of the anticoagulant around the arcuate path adjacent the internal surface of the hollow conduit.

2. An anticoagulant delivery device as defined in claim 1 further comprising a mixing chamber interposed between the perforated tip and the hollow conduit, the mixing chamber comprising means to develop turbulence sufficient to mix the aspirated blood and anticoagulant.

3. An anticoagulant delivery device as defined in claim 1 wherein said channel is annular in configuration and delivers anticoagulant along substantially the entire internal periphery of the hollow conduit in the vicinity of the tip.

4. An anticoagulant delivery device for aspirating and treating blood during surgery comprising:

a hollow conduit, the hollow of the conduit having a vacuum applied thereto and defining a pathway for the transport of aspirated blood;

a perforated tip joined to the conduit and comprising a passageway facilitating aspiration of blood into the hollow of the conduit;

a mixing chamber interposed between the conduit and the perforated tip and having a pathway for aspirated blood which is coextensive with the hollow of the conduit;

a channel traversing the interior periphery of the pathway and opening into the pathway along essentially its entire length; and means for delivering anticoagulant only into the channel so that the anticoagulant will flow radially into the aspirated blood along the length of the open channel.

* * * * *